(12) United States Patent
Gote et al.

(10) Patent No.: US 8,871,476 B2
(45) Date of Patent: Oct. 28, 2014

(54) PROCESS FOR PRODUCTION OF FRUCTO-OLIGOSACCHARIDES

(75) Inventors: Manoj Gote, Pune (IN); Ganapathi Patil, Pune (IN); Maheswaran Palamalai, Pune (IN); Saravanan Rengarajan, Pune (IN); Uday Kashinath Avalakki, Pune (IN)

(73) Assignee: TATA Chemicals Limited, Mumbai (IN)

( * ) Notice: Subject to any disclaimer, the term of this patent is extended or adjusted under 35 U.S.C. 154(b) by 0 days.

(21) Appl. No.: 13/501,076

(22) PCT Filed: Oct. 11, 2010

(86) PCT No.: PCT/IN2010/000674
§ 371 (c)(1),
(2), (4) Date: May 16, 2012

(87) PCT Pub. No.: WO2011/051965
PCT Pub. Date: May 5, 2011

(65) Prior Publication Data
US 2012/0276597 A1 Nov. 1, 2012

(30) Foreign Application Priority Data
Oct. 9, 2009 (IN) .......................... 2360/MUM/2009

(51) Int. Cl.
*C12P 19/02* (2006.01)
(52) U.S. Cl.
USPC ....................................................... 435/105
(58) Field of Classification Search
None
See application file for complete search history.

(56) References Cited

U.S. PATENT DOCUMENTS 4,326,036 A * 4/1982 Hayes ........................... 435/161
4,663,284 A * 5/1987 Jeffries ......................... 435/161

FOREIGN PATENT DOCUMENTS

GB    2179946    3/1987

OTHER PUBLICATIONS

Leathers, Bioconversion of maize residues to value-added coproducts using yeast-like fungi, FEMS Yeast Research 3 (2003) 133-140.*
Yun, Fructooligosaccharides—Occurrence, preparation, and application, Enzyme and Microbial Technology, 19: 107-117, 1996.*
Abouzied M et al, "Direct Fermentation of Potato Starch to Ethanol by Cocultures of *Aspergillus niger* and *Saccharomyces cerevisiae*" Applied and Environmental Microbiology, Nov. 1986, p. 1055-1059.
Jung KH et al, "Production of high fructo-oligosaccharide syrup with two enzyme system of fructosyltransferase and glucose oxidase" Biotechnology Letters, vol. 15 No. 1 (Jan. 1993) pp. 65-70.
Sirisansaneeyakul S. et al, "Enzymatic Production of Fructo-Oligosaccharides from Sucrose", Kasetsart J. (Nat. Sci.) (2000) vol. 34 p. 262-269.
Yang YL et al,, Preparation of High Purity Fructo-oligosaccharides by *Aspergillus japonicas* β-Fructofuranosidase and Successive Cultivation with Yeast, J. Agric. Food Chem. (2008), vol. 56, No. 8, p. 2805-2809.
Yun JW et al, "Semibatch Production of Fructo-Oligosaccharides from Sucrose by Immobilized Cells of *Aureobasidium pullulans*", Applied Biochemistry and Biotechnology vol. 24-25 (1990) p. 299-308.
International Search Report issued in PCT/IN2010/000674, dated Apr. 12, 2011, 4 pages.

* cited by examiner

*Primary Examiner* — Suzanne M Noakes
*Assistant Examiner* — Stephen Chong
(74) *Attorney, Agent, or Firm* — Klarquist Sparkman, LLP

(57) ABSTRACT

A microbial consortium comprises of an *Aureobasidium* sp. to metabolise a sugar substrate into fructooligosaccharide, glucose and fructose and a *Pachysolen* sp to metabolise the glucose and the fructose into ethanol.

9 Claims, 4 Drawing Sheets

FOS concentration is 78.9%

| Index | Name | Time [Min] | Height [µV] | Area [µV Sec] | Area % [%] | As. USP |
|---|---|---|---|---|---|---|
| 1 | GF3 | 5.467 | 20523.8 | 385992.1 | 53.688 | 0.76 |
| 2 | GF2 | 5.775 | 13187.2 | 256859.9 | 35.727 | 2.46 |
| 3 | Sucrose | 6.333 | 1849.1 | 50362.6 | 7.005 | 4.25 |
| 4 | Glucose | 7.417 | 347.1 | 6311.3 | 0.878 | 1.02 |
| 5 | Fructose | 8.850 | 211.5 | 3539.1 | 0.492 | 1.02 |
| 6 | UNKNOWN | 10.467 | 968.6 | 15889.4 | 2.210 | 1.11 |
| Total | | | 37087.4 | 718954.4 | 100.000 | |

FOS percentage in concentrated syrup is 89%

PROCESS FOR PRODUCTION OF FRUCTO-OLIGOSACCHARIDES

CROSS REFERENCE TO RELATED APPLICATIONS

This is the U.S. National Stage of International Application No. PCT/IN2010/000674, filed Oct. 11, 2010, which was published in English under PCT Article 21(2) which in turn claims the benefit of India Patent Application No. 2360/MUM/2009, filed in India on Oct. 9, 2009. Both applications are incorporated by reference herein.

The disclosure generally relates to a method for the production of fructo-oligosaccharide (FOS). More particularly the disclosure relates to a method for production of high purity fructo-oligosaccharide by microbial transformation.

BACKGROUND

Fructo-oligosaccharides are a class of non-digestible carbohydrates or sugars that occur naturally in a wide variety of foods. Fructo-oligosaccharides are composed of glucose units, to which are bound one, two, three or four fructose units. Fructo-oligosaccharides may be trisaccharides (GF2, 1-kestose), tetrasaccharides (GF3, nystose) and pentasaccharides (GF4 (fructofuranosil nystose). These sugars can be found in large quantities in foods such as asparagus, banana, garlic, onion, tomato and wheat.

Fructo-oligosaccharides are commercially available as a nutritional supplement and has a Generally Recognized as Safe (GRAS) status. Fructo-oligosaccharides have about half the natural sweetness of sugar but provide almost no calories since they cannot be digested by humans. Because of these properties fructo-oligosaccharides are used as an artificial sweetening agent in cookies, cakes, breads, candies, dairy products and some drinks. Fructo-oligosaccharides are also used as flavor enhancer, bulking agent and humectants.

Since they are non-digestible, fructo-oligosaccharides pass through the human digestive system virtually unchanged. When these sugars reach the colon, they are utilized by the beneficial bacteria (known as Bifidobacteria or Bifidus) found in the colon for growth and multiplication. This enhances digestion, helps in detoxification and elimination processes, and helps to boost the immune system. Moreover, fructo-oligosaccharides decrease the pH of the intestinal content which helps in calcium and magnesium absorption.

Fructo-oligosaccharides may be produced from sucrose via a transformation reaction catalyzed by a beta-fructofuranosidase/fructosyltransferase enzyme. This enzyme catalyses the transfer of a fructosyl group from a donor to a receptor, which may be sucrose or a fructo-oligosaccharides, such as kestose, nystose to form fructo-oligosaccharides.

The beta-fructofuranosidase/fructosyltransferase enzyme used in the production of fructo-oligosaccharides may be obtained from the cultures of fungi different species, such as (*Aspergillus, Pennicillium, Fusarium, Gloesporium*), from the cultures of yeasts, such as (*Saccharomyces, Rhodotorulla, Pichia, Hansenula, Candida* and *Aureobasidium*), and from some plants, such as asparagus. Whole microbial cells or isolated enzyme may be used for the production of fructo-oligosaccharides.

However, fructo-oligosaccharides that are produced by such methods contain certain amounts of free glucose and fructose in addition to the fructo-oligosaccharides. Therefore, to get high content fructo-oligosaccharides, additional separation processes are needed which adds to the cost of the product. Moreover, the glucose and fructose obtained tend to adversely affect the purity of the fructo-oligosaccharides and also inhibit the bioconversion to fructo-oligosaccharides.

Therefore, there is a need for a process for the production of fructo-oligosaccharides that allows for high yield of high purity fructo-oligosaccharides.

BRIEF DESCRIPTION OF TABLES

Table 1, tabulates the media composition for inoculum preparation of *Aureobasidium pullulans*.

Table 2, tabulates the media composition for liquid culture medium of *Aureobasidium pullulans*.

Table 3, tabulates the conditions for the growth of *Aureobasidium pullulans*.

Table 4, tabulates the media composition for inoculum build and culture medium of *Pachysolen tannophilus*.

Table 5, tabulates the conditions for the growth of *Pachysolen tannophilus*.

Table 6, tabulates the growth and enzyme production by the *Aureobasidium pullulans* at various pH.

Table 7, tabulates the growth and enzyme production by the *Aureobasidium pullulans* at various temperatures.

BRIEF DESCRIPTION OF ACCOMPANYING DRAWINGS

The accompanying drawings illustrate the preferred embodiments of the invention and together with the following detailed description serves to explain the principles of the invention.

SUMMARY

Figure 1:
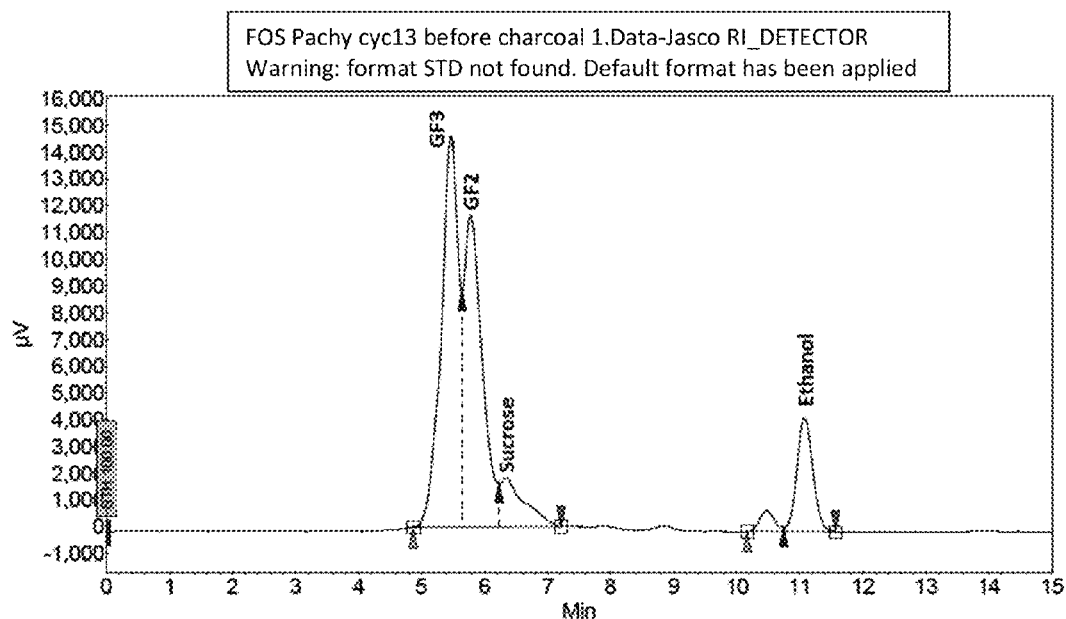
FIG. 1 illustrates a HPLC chromatogram of a sample of final reaction mixture of fructo-oligosaccharides obtained after separation of cells.

A microbial consortium for metabolising a sugar substrate is disclosed. The microbial consortium comprises of an *Aureobasidium* sp. to metabolise a sugar substrate into fructooligosaccaride, glucose and fructose and a *Pachysolen* sp to metabolize the glucose and the fructose into ethanol.

In accordance with an aspect, a process for preparing a microbial consortium is disclosed. The process includes culturing cells of *Aureobasidium* sp in a fermentation medium having pH 4.5 to 6.5, culturing cells of *Pachysolen* sp in a fermentation medium having pH 6.4 to 6.8 and separating the cells of *Aureobasidium* sp and *Pachysolen* sp from their fermentation mediums and mixing the two in a ratio of 1:5 to 1:20 by weight.

In accordance with an aspect, a process for production of fructo-oligosaccharides from a sugar substrate is disclosed. The process includes adding a microbial consortium to the sugar substrate to metabolize sugar substrate into fructo-oligosaccharide, glucose and fructose by *Aureobasidium* sp and further conversion of glucose and fructose to ethanol by *Pachysolen* sp.

DETAILED DESCRIPTION

To promote an understanding of the principles of the invention, reference will be made to the embodiment illustrated in the drawing and specific language will be used to describe the same. It will nevertheless be understood that no limitation of scope of the invention is thereby intended, such alterations and further modifications in the described method and such further applications of the principles of the inventions as illustrated therein being contemplated as would normally occur to one skilled in art to which the invention relates.

A microbial consortium for the production of fructo-oligosaccharides is disclosed. The microbial consortium comprises of microorganisms of *Aureobasidium* sp and *Pachysolen* sp. In accordance with an aspect, the microorganism may be wild type or mutants. In accordance with an embodiment, the consortium comprises of *Aureobasidium pullulans* and *Pachysolen tannophilus*.

A process for the production of the microbial consortium for the production of fructo-oligosaccharides is disclosed. The process comprises of obtaining cell mass of the microorganisms by culturing the cells of *Aureobasidium* sp and *Pachysolen* sp in a suitable medium, separating the cells of *Aureobasidium* sp and *Pachysolen* sp from the culture medium and combining the separated microbial cells in a specified ratio to obtain a microbial consortium for the production of fructo-oligosaccharides.

In accordance with an aspect, an inoculum of *Aureobasidium* sp is first prepared by culturing the cells of *Aureobasidium* sp in a suitable medium. By way of a specific example and as tabulated in table 1, the medium for preparation of inoculum of *Aureobasidium pullulans* comprises of 1.0 percent glucose, 0.30 percent yeast extract, 0.50 percent peptone and 100 ml distilled water. The pH of the medium for preparation of inoculum of *Aureobasidium pullulans* is maintained at 6.5±0.5.

Once prepared, the inoculum of *Aureobasidium* sp is used to inoculate a liquid culture medium that allows maximum production of the enzyme beta-fructofuranosidase in the cells of *Aureobasidium* sp. By way of a specific example and as tabulated in table 2, the liquid culture medium comprises of 5.0 to 10.0 percent of sucrose, 1.0 to 2.0 percent of yeast extract, 0.25 to 0.5 percent of sodium chloride and 0.1 to 0.3 percent MgSO4, 0.1 to 0.2% K2HPO4 and 0.3-0.5% KH2PO4. In accordance with an aspect 2 to 5 percent inoculum is used to inoculate the liquid culture medium.

In accordance with an aspect the *Aureobasidium* sp is cultured at a temperature in the range of 27 to 29° C., pH in the range of 5.5 to 6.5 for a period of 48 to 72 hrs. The cells are agitated at a speed in the range from 180 to 200 revolutions per minute. Table 3 tabulates the conditions for growth of *Aureobasidium pullulans*.

The biomass of *Pachysolen* sp. is also produced by culturing the cells of *Pachysolen* sp. in a suitable medium till the required cell mass is obtained. By way of a specific example cell mass of *Pachysolen* sp. is produced by growing the cells of *Pachysolen* sp in a liquid culture medium containing 0.1 to 0.3 percent malt extract, 1.0 to 2.0 percent glucose, 0.1 to 0.3 percent yeast extract and 0.25 to 0.5 percent peptone. Table 4 tabulates the composition of the medium for culturing of *Pachysolen* sp. The same medium may be used for preparing the inoculum and for culturing the cells. In accordance with an aspect *Pachysolen* sp. may be cultured at a temperature in the range of 27 to 29° C., a pH in the range of 6.4 to 6.8, for a period of 48 to 72 hrs. The cells may be agitated at a speed in the range of 180 to 200 revolutions per minute.

The microbial cells obtained by culturing the cells of *Aureobasidium* sp and *Pachysolen* sp. are then separated from the respective cultural media. The microbial cells may be separated by any separation means including but not limited to filtration, tangential filtration method, decanting or their combination. In accordance with an aspect, the microbial cells of *Pachysolen* sp. are separated from the culture medium by tangential filtration method using hollow fiber membrane filter having 0.2 to 0.5μ pore size followed by centrifugation at 4000 to 10000 RPM. In accordance with an aspect, the microbial cells of *Aureobasidium* sp. are separated from the culture medium by simple dead end filtration method using 0.5 to 1.0μ pore size filter pads.

The microbial consortium is obtained by combining the cells of the *Aureobasidium* sp and *Pachysolen* sp. In accordance with an aspect, the weight of the cell mass of the *Aureobasidium pullulans* used in the consortium depends up on the enzyme activity present in the cell mass. By way of a specific example, for cells having an enzyme activity of approximately 400-500 enzyme units per gram of the weight/weight cell mass of *Aureobasidium pullulans* in the consortium is in the range of 0.5 to 1.0 percent. The weight of *Pachysolen* in the consortium is in the range of 5 to 10 percent on weight/weight basis.

A process for the production of fructo-oligosaccharides is disclosed. More particularly the process for the production of fructo-oligosaccharides by biotransformation of sucrose is disclosed.

The process of the production of fructo-oligosaccharides comprises of reacting sucrose with a microbial consortium comprising of *Aureobasidium* sp. and *Pachysolen* sp. to obtain fucto-oligosaccharides.

The process comprises of reacting a sucrose solution with mycelia bound beta-fructofuranosidase enzyme in the *Aureobasidium* sp. cells to obtain a mixture of fructo-oligosaccharide, glucose and fructose, and fermenting the glucose and fructose in the mixture to ethanol by contacting the mixture with cells of a xylose fermenting yeasts, *Pachysolen* sp to obtain fructo-oligosaccharide.

The process further comprises of reacting the microbial consortium comprising of cells of *Aureobasidium* sp. and *Pachysolen* sp with an aqueous sucrose solution as substrate till sucrose is converted into fructo-oligosaccharides. In accordance with an aspect, the concentration of sucrose in the substrate is in the range of 20 to 50 percent (weight/volume). The amount of wet biomass of each microorganism is in the range of 1.0 to 10.0 percent (weight/volume)

The process for the production of fructo-oligosaccharides is carried out at a temperature in the range of 27 to 29° C., and at pH in the range of 4.5 to 6.5.

In accordance with an aspect, after complete conversion of sucrose to fructo-oligosaccharides and ethanol the reaction is terminated and the fermented medium containing fructo-oligosaccharides and ethanol is separated from the microbial cells. In accordance with an aspect the fermented medium may be separated from the microbial cells by any means including but not limited to filtration, centrifugation, decanting or their combination. In accordance with an embodiment the fermented medium is separated from microbial cells using hollow fiber membrane filter having 0.2 to 0.5μ pore size.

In accordance with an aspect, after the separation of microbial cells fructo-oligosaccharides and ethanol mixture is treated with activated charcoal to remove the color and protein impurities. The charcoal added is in the range of 1-2% w/v. For example, 2 gm of charcoal may be used for 100 ml of fructo-oligosaccharides. In accordance with an aspect, the activated charcoal is reacted with fructo-oligosaccharides and the ethanol while maintaining the pH in the range of 5.5-6.5. The treatment with activated charcoal may be carried out for 3 to 5 hours. The charcoal may be separated by filtration or by simple charcoal filter pads or sparkler filter.

Fructo-oligosaccharides may be recovered from the fermented medium by any known method. In accordance with an aspect the separation of fructo-oligosaccharide from the ethanol may be carried out by methods including but not limited to vacuum concentration, evaporation method or their combination.

In accordance with an aspect, the microbial cells may be reused for the production of fructo-oligosaccharides by reacting them with fresh substrate comprising of sucrose in water.

EXAMPLE

The following examples are provided to explain and illustrate certain preferred embodiments of the process of the invention.

pH Optimization for the Growth and Maximal Enzyme Production by the *Aureobasidium pullulans*:

Cells of *Aureobasidium pullulans* were grown at various pHs viz. 4.5, 5.0, 5.5, 6.0, 6.5 and 7.0 etc. and checked for the cell mass grams (weight/weight) per liter of medium and enzyme activity enzyme Unit/gram (weight/weight) of biomass. As tabulated in table 6, *Aureobasidium pullulans* grows in the pH range 4.5 to 6.5 and produces similar quantity of enzyme per g (w/w) of biomass. However, the maximal cell mass is obtained at pH 4.5.

Temperature Optimisation for the Growth and Maximal Enzyme Production by the *Aureobasidium pullulans*:

*Aureobasidium pullulans* culture was grown at various temperatures viz. 25, 30 & 35° C. etc. and checked for the cell mass grams (weight/weight) per liters of medium and enzyme activity enzyme Units/gram (w/w) of biomass. As tabulated in table 7, results indicate that *Aureobasidium pullulans* grows in the temperature range 25-30° C. However, it will not grow at and above 35° C.

Figure 2:
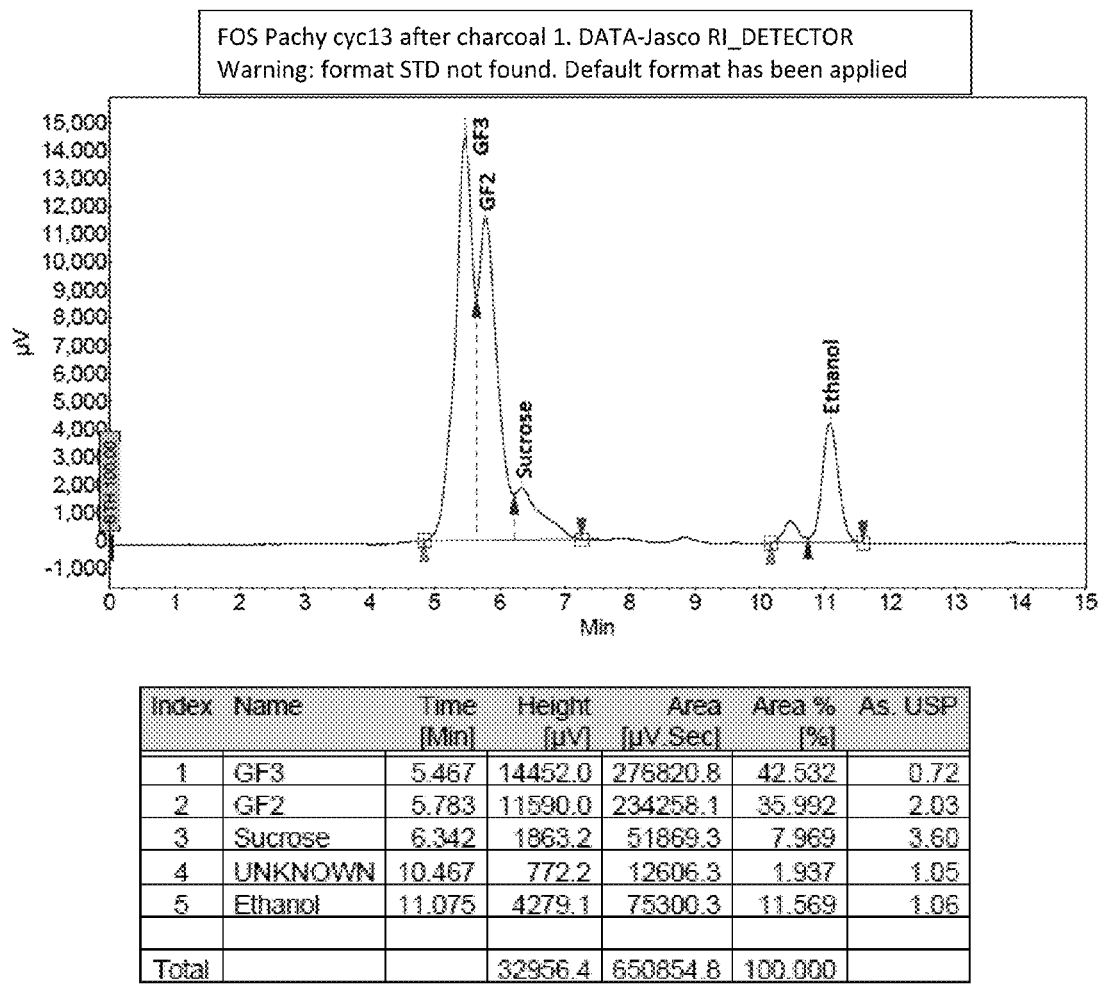
FIG. 2 illustrates a HPLC chromatogram of a sample of final reaction mixture of fructo-oligosaccharides obtained after charcoal treatment.
Figure 3:
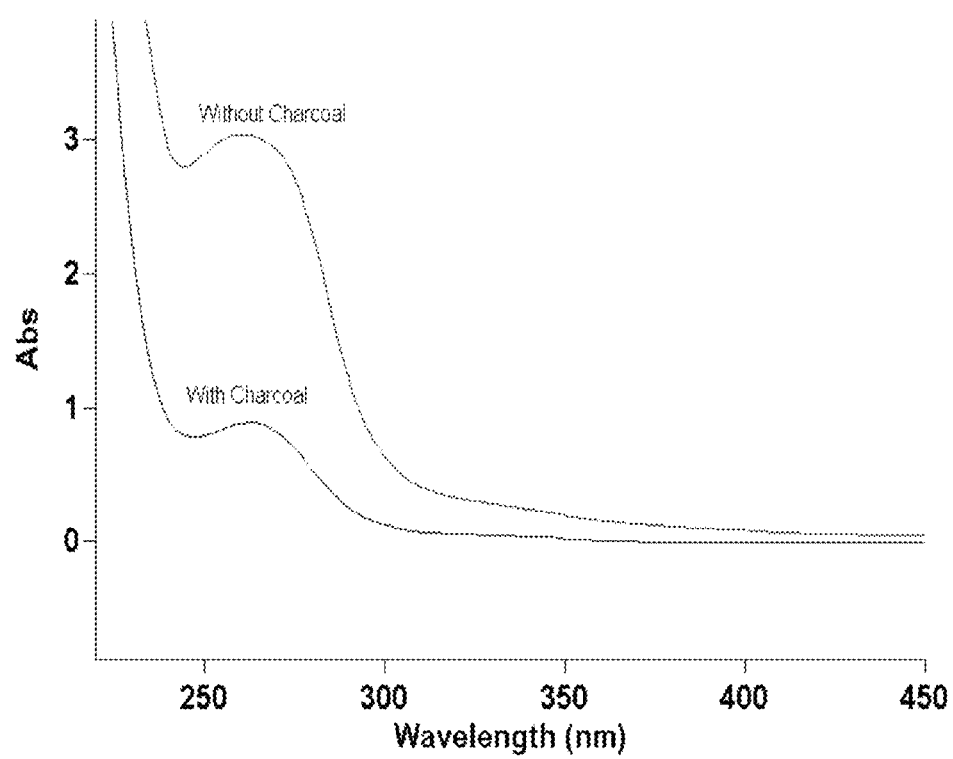
FIG. 3 illustrates the scan spectra of the sample before and after charcoal treatment, showing the reduction of protein and color impurities.
Figure 4:
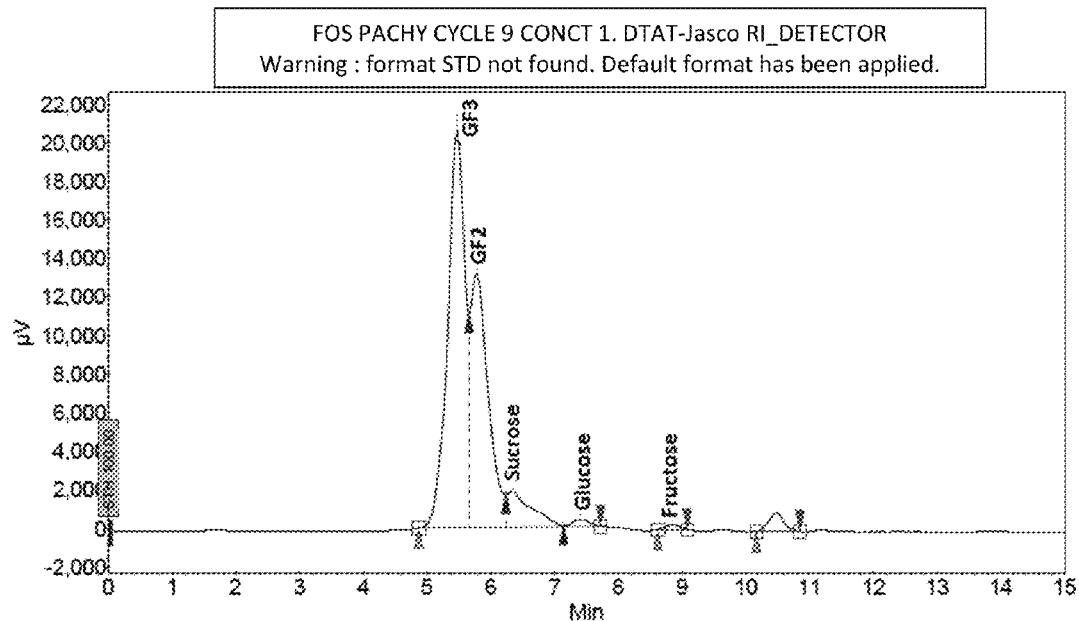
FIG. 4 illustrates a HPLC chromatogram of a sample of the final concentrated fructo-oligosaccharides solution.

Charcoal Treatment for the Removal of Color and Protein Impurities from the Fructo-Oligosaccharides Samples:

Fructo-oligosaccharides sample after separation of microorganisms was treated with activated charcoal 1.0 to 2.0% and at pH 5.5-6.5. The mixture was kept at room temperature under continuous stirring for 3.0 to 5.0 hrs. At the end of incubation the charcoal was separated by filtration with charcoal filter pads. FIG. 3. illustrates the scan spectra of the sample before and after charcoal treatment, showing the reduction of protein and color impurities. FIG. 2 illustrates the HPLC chromatograph of the sample after the charcoal treatment.

Specific Embodiments are Described Below

A microbial consortium comprising an *Aureobasidium* sp. to metabolise a sugar substrate into fructooligosaccharide, glucose and fructose and a *Pachysolen* sp to metabolise the glucose and the fructose into ethanol.

Such microbial consortium(s), wherein the *Aureobasidium* sp is *Aureobasidium pullulans*.

Such microbial consortium(s), wherein the *Pachysolen* sp is *Pachysolen tannophilus*.

Such microbial consortium(s), wherein the cell mass ratio of *Aureobasidium* sp to *Pachysolen* sp is 1:5 to 1:20.

Such microbial consortium(s), wherein the cells of *Aureobasidium* sp have an enzyme activity in the range of 400-500 enzyme units per gram weight/weight.

A process for preparing a microbial consortium comprising culturing cells of *Aureobasidium* sp in a fermentation medium having pH 4.5 to 6.5, culturing cells of *Pachysolen* sp in a fermentation medium having pH 6.4 to 6.8 and separating the cells of *Aureobasidium* sp and *Pachysolen* sp from their fermentation media and mixing the two in a ratio of 1:5 to 1:20 by weight.

Such process(s), wherein the fermentation medium for *Aureobasidium* sp is a liquid culture medium comprising of 5-10% sucrose, 1-2% yeast extract, 0.25-0.5% sodium chloride, 0.1-0.3% magnesium sulphate and 0.1-0.2% dipotassium phosphate and 0.3-0.5% monopotassium phosphate.

Such process(s), wherein the fermentation medium for *Pachysolen* sp is a liquid culture medium comprising of 0.1-0.3% malt extract, 1-2% glucose, 0.1-0.3% yeast extract and 0.25-0.5% peptone.

Such process(s), wherein culturing cells of *Aureobasidium* sp in the fermentation medium is done at temperature in the range of 27-29° C.

Such process(s), wherein culturing cells of *Pachysolen* sp in the fermentation medium is done at temperature in the range of 27-29° C.

A process for production of fructo-oligosaccharides from a sugar substrate comprising adding a microbial consortium to the sugar substrate, wherein the microbial consortium comprises of an *Aureobasidium* species to metabolise the sugar substrate into fructooligosaccharide, glucose and fructose and a *Pachysolen* species to convert the glucose and the fructose into ethanol.

Such process(s), wherein the cell mass ratio of *Aureobasidium* sp and *Pachysolen* sp in the microbial consortium is in the range of 1:5 to 1:20.

Such process(s), further comprising separating the microbial consortium from fructo-oligosaccharides and ethanol.

Such process(s), further comprising separating the fructo-oligosaccharides from ethanol by any of vacuum filtration or evaporation method or any combination thereof.

Such process(s), wherein the fructo-oligosaccharides and ethanol is treated with activated charcoal to remove color and protein impurities.

Such process(s), wherein the activated charcoal is used in concentration range of 1 to 2% w/v.

Such process(s), further comprising recycling the separated microbial consortium by adding it to a sugar substrate for obtaining fructo-oligosaccharides.

Such process(s), wherein the sugar substrate is an aqueous solution of sucrose having concentration in the range of 20-50% w/v.

Such process(s), wherein the microbial consortium and the sugar substrate are held for 24-36-hours at temperature in the range of 27-29° C.

INDUSTRIAL APPLICABILITY

The process as disclosed allows for production of high purity fructo-oligosaccharides in a simple and efficient manner. The process uses microbial cells, is easy to carry out and is of low cost. Moreover, the process disclosed excludes costly and time consuming downstream process requirement for removal of unwanted sugars.

Referring to the FIGS. 1 and 2, the process allows for the production of fructo-oligosaccharides, including trisaccharide (GF2 1-kestose) and tetrasaccharide (GF3, nystose). Moreover, the process allows for the production of fructo-oligosaccharides, where concentration of tetrasaccharide (GF3, nystose) is greater than or equal to trisaccharide (GF2 1-kestose). The purity of fructo-oligosaccharides obtained by this process is in the range of 90 to 95 percent. Moreover, a yield in the range of 60 to 70 percent on the basis of weight is obtained using the process as disclosed.

Furthermore, process disclosed provides production of fructo-oligosaccharides in highly purified form, since the *Pachysolen* sp metabolises the glucose and fructose produced by *Aureobasidium* sp., into ethanol, thereby increasing the concentration of fructo-oligosaccharides in the final product. The conversion of the glucose and the fructose into ethanol also simplifies downstream processing and improves purity of fructo-oligosaccharides recovered.

In addition, the treatment of mixture of fructo-oligosaccharides and ethanol with charcoal further purifies the mixture thereby producing purified fructo-oligosaccharides.

By way of a specific example, a sample of the final reaction mixture of fructo-oligosaccharides was separated from the cells and a 5 μl dilute sample was analysed using HPLC (Jasco) sugar analysis column (Sodex SC 1011). Peaks were identified using authentic samples and the percentage of fructo-oligosaccharides in the sample was calculated from the peak area. The concentration of fructo-oligosaccharides in the sample was observed to be 78.9 percent. The chromatogram of the sample is illustrated in FIG. 1.

By way of a further specific example, a 5 μl dilute sample of the final reaction mixture of fructo-oligosaccharides was separated from the cells after charcoal treatment was analysed using HPLC (Jasco) sugar analysis column (Sodex SC 1011). Peaks were identified using authentic samples and the percentage of fructo-oligosaccharides in the sample was calculated from the peak area. The concentration of fructo-oligosaccharides was observed to be 78.4 percent. The chromatogram of the sample is illustrated in FIG. 2.

By way of a further specific example, a sample of concentrated fructo-oligosaccharides after separating fructo-oligosaccharides from fructo-oligosaccharides and ethanol solution was analysed. A 5 μl dilute sample was applied to HPLC (Jasco) on a sugar analysis column (Sodex SC 1011) and peaks were identified using authentic samples. The percentage of fructo-oligosaccharides in the sample was calculated from the peak area. The concentration of fructo-oligosaccharides in the sample was observed to be 89 percent on the basis of volume.

TABLE 1

Media composition for the inoculum preparation of *Aureobasidium pullulans*

| Sr. No. | Components | Value |
|---|---|---|
| 1 | Glucose | 1.0% |
| 2 | Yeast extract | 0.30% |
| 3 | Peptone | 0.50% |
| 4 | D/W | 100 ml |
| 7 | pH | 6.5 ± 0.5 |

TABLE 2

Media composition for the liquid culture medium *Aureobasidium pullulans*

| Sr. No. | Components | Value |
|---|---|---|
| 1 | Sucrose | 5.00% |
| 2 | Yeast extract | 1.0% |
| 3 | $K_2HPO_4$ | 0.10% |
| 4 | $KH_2PO_4$ | 0.50% |
| 5 | NaCl | 0.25% |
| 6 | $MgSO_4 \cdot 7H_2O$ | 0.20% |
| 7 | pH | 5.5-6.5 |

TABLE 3

Conditions for the growth of *Aureobasidium pullulan*:

| Sr. No. | Components | Value |
|---|---|---|
| 1 | Temp. | 27-29° C. |
| 2 | pH | 5.5-6.5 |
| 3 | Aeration | — |
| 4 | Aggitation | 180-200 RPM |
| 5 | Inoculum | 2-5% |

TABLE 4

Media composition for the inoculum build and fermentation medium of *Pachysolen tannophilus*:

| Sr. No. | Components | Value |
|---|---|---|
| 1 | Malt extract | 0.30% |
| 2 | Glucose | 1.00% |
| 3 | Yeast extract | 0.30% |
| 4 | Peptone | 0.50% |
| 5 | D/M | 100 ml |
| 6 | pH | 6.4-6.8 |

TABLE 5

Conditions for the growth of *Pachysolen tannophilus*:

| Sr. No. | Components | Value |
|---|---|---|
| 1 | Temp. | 27-29° C. |
| 2 | pH | 6.4-6.8 |
| 3 | Aggitation | 180-200 RPM |
| 4 | Inoculum | 2-5% |

TABLE 6 pH optimum for the growth and maximal enzyme production by the *Aureobasidium pullulans*

| Ph | Biomass grams (w/w)* | Enzyme activity Units /gram biomass | Total activity |
|---|---|---|---|
| 4.5 | 3.25 g | 430.88 | 1420.61 |
| 5.0 | 3.0 g | 440.88 | 1340.64 |
| 5.5 | 1.98 g | 440.6 | 820.36 |
| 6.0 | 1.73 g | 450.4 | 780.54 |
| 6.5 | 1.52 g | 440.6 | 670.79 |
| 7.0 | 1.34 g | 370.2 | 490.84 |

TABLE 7

Temperature optimum for the growth and maximal enzyme production by the *Aureobasidium pullulans*

| Temp. ° C. | Biomass grams (w/w)* | Enzyme activity Units/gram biomass | Total activity |
|---|---|---|---|
| 25 ° C. | 2.40 g | 440.75 | 1070.40 |
| 30 ° C. | 1.85 g | 430.86 | 810.14 |
| 35 ° C. | 0.25 g | 50.16 | 10.29 |

We claim:

1. A process for production of fructo-oligosaccharides from a sugar substrate, comprising:

adding a microbial consortium to the sugar substrate, wherein the microbial consortium comprises an *Aureobasidium* species to metabolise the sugar substrate into fructo-oligosaccharide, glucose, and fructose; and a *Pachysolen* species to convert the glucose and the fructose into ethanol.

2. A process as claimed in claim 1, wherein the cell mass ratio of the *Aureobasidium* species and the *Pachysolen* species in the microbial consortium is in the range of 1:5 to 1:20.

3. A process as claimed in claim 1 further comprising separating the microbial consortium from fructo-oligosaccharides and ethanol.

4. A process as claimed in claim 3 further comprising separating the fructo-oligosaccharides from ethanol by any of vacuum filtration or evaporation method or any combination thereof.

5. A process as claimed in claim 3 wherein the fructo-oligosaccharides and ethanol is treated with activated charcoal to remove color and protein impurities.

6. A process as claimed in claim 5 wherein the activated charcoal is used in concentration range of 1 to 2% w/v of fructo-oligosaccharides.

7. A process as claimed in claim 3, further comprising recycling the separated microbial consortium by adding it to a sugar substrate for obtaining fructo-oligosaccharides.

8. A process as claimed in claim 1, wherein the sugar substrate is an aqueous solution of sucrose having concentration in the range of 20-50% w/v.

9. A process as claimed in claim 1, wherein the microbial consortium and the sugar substrate are held for 24-36 hours at temperature in the range of 27-29° C.

\* \* \* \* \*